United States Patent [19]

Hamprecht et al.

[11] 4,183,949
[45] Jan. 15, 1980

[54] PESTICIDALLY ACTIVE 1-ARYLAMINO-2,4-DINITRONAPHTHALENES

[75] Inventors: Rainer Hamprecht, Cologne; Alfons Hartmann, Beckingen; Erich Klauke, Odenthal-Hahnenberg; Ingeborg Hammann, Cologne; Peter Roessler, Bergisch-Gladbach; Wilhelm Brandes, Cologne, all of Fed. Rep. of Germany

[73] Assignee: Bayer Aktiengesellschaft, Leverkusen, Fed. Rep. of Germany

[21] Appl. No.: 876,456

[22] Filed: Feb. 1, 1978

[30] Foreign Application Priority Data

Feb. 26, 1977 [DE] Fed. Rep. of Germany ....... 2708440

[51] Int. Cl.$^2$ .................. A01N 9/20; C07C 87/66; C07C 121/78
[52] U.S. Cl. ................... 424/304; 260/205; 260/340.3; 260/465 E; 260/508; 260/558 P; 260/562 P; 260/576; 424/226; 424/278; 424/309; 424/315; 424/324; 424/330; 560/21
[58] Field of Search ............ 260/465 E, 576; 424/304, 330, 226, 278, 309, 315, 324

[56] References Cited

U.S. PATENT DOCUMENTS

3,950,377 4/1976 Barlow ............................ 260/465 E

OTHER PUBLICATIONS

Mangini et al., Chemical Abstracts, vol. 32, 1258 (1938).

H. J. van Opstall, Chemical Abstracts, vol. 28, 26 (1934).

Kawasaki et al., Chemical Abstracts, vol. 77, 39722b (1972).

*Primary Examiner*—Dolph H. Torrence
*Attorney, Agent, or Firm*—Sprung, Felfe, Horn, Lynch & Kramer

[57] ABSTRACT

1, Arylamino-2,4-dinitronaphthalenes of the formula

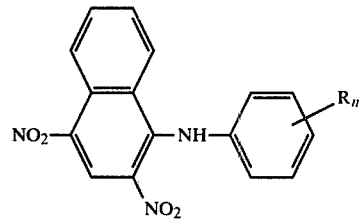

in which
R each independently is hydrogen, alkyl, halogenoalkyl, alkenyl, alkynyl, alkoxy, alkylmercapto, alkylsulphonyl, sulphonate, halogenoalkoxy, halogenoalkylmercapto, acylamino, alkoxycarbonyl, phenylazo, halogen, CN or nitro, or two radicals R in orthoposition to one another can, conjointly with the two adjoining carbon atoms of the phenyl ring, form an optionally halogen-substituted 1,3-dioxane ring, and
n is 1,2,3,4 or 5 which possess arthropodicidal, fungicidal and bactericidal properties.

10 Claims, No Drawings

PESTICIDALLY ACTIVE 1-ARYLAMINO-2,4-DINITRONAPHTHALENES

The present invention relates to and has for its objects the provision of particular new 1-arylamino-2,4-dinitronaphthalenes which possess arthropodicidal, fungicidal and bactericidal properties, active compositions in the form of mixtures of such compounds with solid and liquid dispersible carrier vehicles, and methods for producing such compounds and for using such compounds in a new way especially for combating pests, e.g. arthropods, fungi and bacteria, with other and further objects becoming apparent from a study of the within specification and accompanying examples.

It has already been disclosed that arylaminonaphthalenes, of which the naphthyl radical is substituted by halogen, exhibit insecticidal, acaricidal, fungicidal and bactericidal properties. Their action, however, is not fully satisfactory, especially if low amounts are used (see German Offenlegungsschrift (German Published Specification) No. 2,213,058).

The present invention provides, as new compounds, the 1-arylamino-2,4-dinitronaphthalenes of the general formula

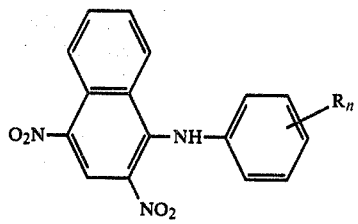

in which
n is 1, 2, 3, 4 or 5 and
R represents hydrogen, alkyl, halogenoalkyl, alkenyl, alkynyl, alkoxy, alkylmercapto, alkylsulphonyl, sulphonate, halogenoalkoxy, halogenoalkylmercapto, acylamino, phenylazo, halogen, CN, $NO_2$ or alkoxycarbonyl, the radicals R being selected independently of one another when n is 2 or more, and two radicals R, in the ortho-position to one another, conjointly with the two adjoining carbon atoms of the phenyl ring, can form an optionally halogen-substituted 1,3-dioxane ring.

Preferably, each R is selected independently from hydrogen, alkyl with 1–4 carbon atoms (especially methyl), alkoxy with 1–4 carbon atoms, alkylmercapto with 1–4 carbon atoms, alkylsulphonyl with 1–4 carbon atoms, sulphonate (especially sodium sulphonate), halogenoalkyl, halogenoalkoxy or halogenoalkylmercapto each with 1–4 carbon atoms and with 3–5 halogen atoms, acylamino such as lower alkanoylamino with 1–4 carbon atoms and optionally halogen substituted or aroylamino such as benzoylamino, methoxycarbonyl, phenylazo, halogen, CN and $NO_2$, or two radicals R in the ortho-position to one another, conjointly with the two adjoining C atoms of the phenyl ring, form a 1,3-dioxane ring which is optionally substituted by fluorine.

Surprisingly, the 1-arylamino-2,4-dinitronaphthalenes of the present invention show a substantially higher insecticidal, acaricidal, development-inhibiting, fungicidal and bactericidal potency than the known halogen-substituted arylaminonaphthalenes which are chemically the nearest compounds of the same type of action. The compounds according to the invention thus represent an enrichment of the art.

The present invention also provides a process for the preparation of a 1-arylamino-2,4-dinitronaphthalene of the formula (I) in which (a) a compound of the general formula

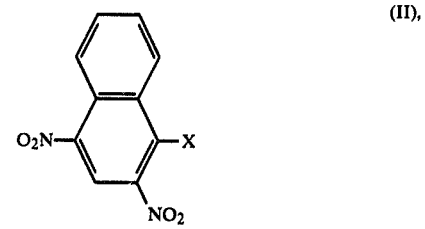

in which
X represents fluorine, chlorine, bromine or an aliphatic or aromatic sulphonic acid ester radical,
is reacted with an aniline of the general formula

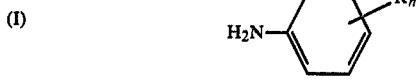

in which
R and n have the above-mentioned meanings,
in the presence of an acid-binding agent and, if appropriate, in the presence of a diluent, or (b) a compound of the general formula

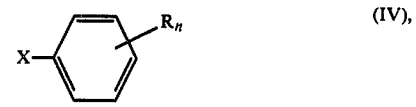

in which
X represents fluorine, chlorine, bromine or an aliphatic or aromatic sulphonic acid ester radical and
R and n have the above-mentioned meanings,
is reacted with 3,4-dinitro-1-naphthylamine, of the formula

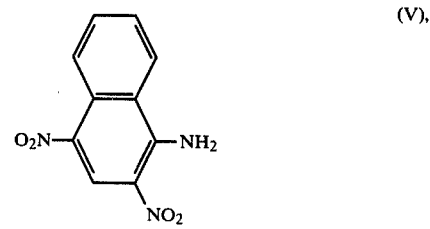

in the presence of an acid-binding agent and, if appropriate, in the presence of a diluent.

If 1-chloro-2,4-dinitronaphthalene and 2,6-dichloro-4-trifluoromethylaniline are used as starting materials, the course of the reaction can be represented by the following equation:

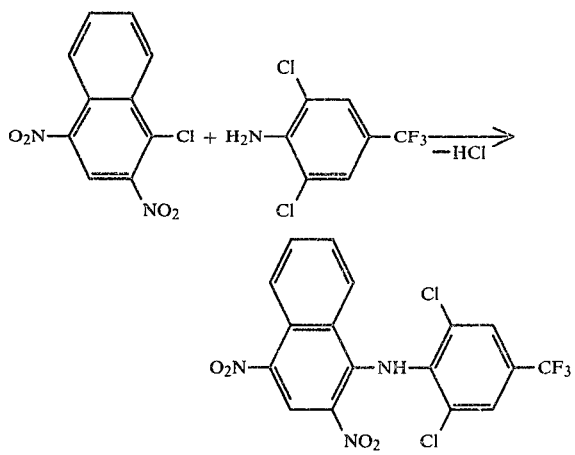

Compounds of the formulae (II), (III), (IV) and (V) to be used as starting materials are known and can be prepared in accordance with known processes.

Particularly preferred compounds are prepared by reacting 1-chloro-2,4-dinitronaphthalene with an aniline of the formula (III), in which each R represents hydrogen, nitro, cyano, methylsulphonyl, sulphonate, trifluoromethyl, trifluoromethylmercapto, trifluoromethoxy, alkyl or alkoxy with 1–4 carbon atoms, acylamino, phenylazo or halogen (such as fluorine, chlorine or bromine) and n represents 1, 2, 3 or 5.

The following may be mentioned as examples of anilines of the formula (III) which can be used according to the invention: 2,4-dichloroaniline, 2,5-dichloroaniline, 2,6-dichloroaniline, 3,4-dichloroaniline, 3,5-dichloroaniline, 3-chloro-4-fluoroaniline, 2,4-difluoroaniline, 2,4,5-trichloroaniline, 2,4,6-trichloroaniline, 4-nitroaniline, 2-chloro-4-nitroaniline, 3-chloro-4-nitroaniline, 4-chloro-2-nitroaniline, 4-chloro-3-nitroaniline, 2,4-dichloro-6-nitroaniline, 2,6-dichloro-4-nitroaniline, 2-bromo-4-nitroaniline, 2-bromo-4,6-dinitroaniline, 2-chloro-4,6-dinitroaniline, 3-chloro-6-methyl-4-nitroaniline, 5-chloro-2-methoxy-4-nitroaniline, 4-methyl-2-nitroaniline, 2,4-dinitroaniline, 2,6-dinitroaniline, methyl 4-amino-2-chloro-benzoate, 4-nitro-2-trifluoromethylaniline, 2-nitro-4-trifluoromethylaniline, 2,4-dinitro-6-trifluoromethylaniline, 3-trifluoromethylaniline, 2,4-bis-trifluoromethylaniline, 3,5-bis-trifluoromethylaniline, 4-chloro-2-trifluoromethylaniline, 4-chloro-3-trifluoromethylaniline, 3-chloro-4-trifluoromethylaniline, 2-chloro-5-trifluoromethylaniline, 2,6-dichloro-4-trifluoromethylaniline, 2,3,5,6-tetrachloro-4-trifluoromethylaniline, 4-trifluoromethoxy-aniline, 3-chloro-4-trifluoromethoxy-aniline, 3-chloro-4-trifluoromethylmercapto-aniline, 6-amino-2,2,4,4-tetrafluoro-1,3-benzodioxane, 2-bromo-4-nitro-6-trifluoromethylaniline, 2-amino-5-nitrobenzonitrile, 2-amino-3,5-dinitrobenzonitrile, 2-amino-3-bromo-5-nitrobenzonitrile, 4-amino-1,3-phthalodinitrile, 2-amino-5-trifluoromethyl-benzonitrile, 4-ethoxyaniline, 4-methoxy-2-nitroaniline, 4-methoxy-3-nitroaniline, 4-methoxy-3-trifluoromethylaniline, 4-amino-3-nitro-azobenzene, 4-amino-3,5-dibromo-azobenzene, 4-methylsulphonylaniline, 2-methylsulphonyl-4-nitroaniline, the sodium salt of 3-amino-benzenesulphonic acid, 3-amino-acetanilide, 4-amino-acetanilide, 4-allyl-aniline and 4-propargyl-aniline.

Suitable diluents for process variants (a) and (b) are inert organic solvents. Preferably, dimethylformamide or tetrahydrofuran is used. At times it is also advantageous to carry out the process in aqueous suspension.

Suitable acid-binding agents are bases, such as alkali metal hydroxides, alkali metal carbonates or alkali metal hydrides. The use of potassium hydroxide or sodium hydride is preferred.

The reaction can also be carried out in a two-phase system with the aid of phase transfer catalysts such as alkyl-ammonium salts or alkylphosphonium salts. In that case, the aqueous phase contains the acid-binding agent (for example potassium hydroxide) and the organic phase (for example toluene) contains the starting materials.

The reaction temperatures can be varied within a substantial range. In general, the reaction is carried out at from −10° to +100°, preferably at from 10° to 40° C.

Usually, the reactants are employed in equimolar amounts, but one or other component can also be used in excess.

As already mentioned, the compounds according to the invention are active as pesticides. They have a powerful fungitoxic and bacteriotoxic action. They do not damage crop plants in the concentrations required for combating fungi and bacteria. For these reasons, they are suitable for use as plant protection agents for combating fungi and bacteria. Fungitoxic agents in plant protection are employed for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or attack the plants through the soil, as well as against seed-borne pathogens.

The active compounds according to the invention exhibit a particularly good activity against parasitic fungi which attack above-ground parts of plants, such as rust diseases of cereals, caused by species of Puccinia, and bean rust (*Uromyces phaseoli*), as well as against powdery mildew caused by species of Erysiphe, and powdery mildew of apples (*Podosphaera leucotricha*) and, in the case of rice, against *Pyricularia oryzae* and *Pellicularia sasakii*. On above-ground parts of plants, the compounds are also active against species of Botrytis, species of Septoria, species of Helminthosphorium and species of Cercospora. The active compounds are effective and of particular practical importance when they are used as seed dressings or soil treatment agents against phytopathogenic fungi which adhere to the seed and occur in the soil, and cause seedling diseases, root rot, tracheomycoses and seed diseases in crop plants, such as species of Fusarium, species of Rhizoctonia, *Verticillium alboatrum* and *Phialophora cinerescens*.

When used in higher amounts, the active compounds according to the invention are also herbicidally active.

The active compounds are well tolerated by plants, have a favorable level of toxicity to warm-blooded animals, and can be used for combating arthropod pests, especially insects and acarids, which are encountered in agriculture, in forestry, in the protection of stored products, and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber*;

from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

In low use concentrations, the active compounds according to the invention exhibit a development-inhibiting activity on some or all stages of development of insects.

When used against hygiene pests and pests of stored products, the active compounds are distinguished by an excellent residual activity on wood and clay as well as a good stability to alkali on limed substrates.

The active compounds according to the instant invention can be utilized, if desired, in the form of the usual formulations or compositions with conventional inert (i.e., plant compatible or herbicidally inert) pesticide diluents or extenders, i.e., diluents, carriers or extenders of the type usable in conventional pesticide formulations or compositions, e.g. conventional pesticide dispersible carrier vehicles such as gases, solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances and in coating compositions, for use on seed, and formulations used with burning equipment, such as fumigating cartridges, fumigating cans, fumigating coils and the like, as well as ULV cold mist and warm mist formulations.

These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as halogenated hydrocarbons, e.g. dichlorodifluoromethane and trichloromethane, as well as butane, propane, nitrogen and carbon dioxide; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as solid carriers, ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules; crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin; hydrolyzates, etc., and especially alkyl arylpolyglycol ethers, magnesium stearate, sodium oleate, etc.); and/or dispersing agents, such as lignin, sulfite waste liquors, methyl cellulose, etc.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

Such active compounds may be employed alone or in the form of mixtures with one another and/or with such solid and/or liquid dispersible carrier vehicles and/or with other known compatible active agents, especially plant protection agents, such as other arthropodicides, fungicides and bactericides, or nematicides, rodenticides, herbicides, fertilizers, growth-regulating agents, etc., if desired, or in the form of particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0000001–100, preferably 0.01–10%, by weight of the mixture. Thus, the present invention contemplates overall compositions which comprise mixtures of a conventional dispersible carrier such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.01–95%, by weight of the mixture.

The active compounds can also be used in accordance with the well known ultra-low-volume process with good success, i.e., by applying such compound if normally a liquid, or by applying a liquid composition containing the same, via very effective atomizing equipment, in finely divided form, e.g. average particle diameter of from 50–100 microns, or even less, i.e., mist form, for example by airplane crop spraying techniques. Only up to at most about a few liters/hectare are needed, and often amounts only up to about 15 to 1,000 g/hectare, preferably 40 to 600 g/hectare, are sufficient. In this process it is possible to use highly concentrated liquid compositions with said liquid carrier vehicles containing from about 20 to about 95% by weight of the active compound or even the 100% active substance alone, e.g. about 20–100% by weight of the active compound.

Furthermore, the present invention contemplates methods of selectively killing, combating or controlling pests, e.g. arthropods, fungi and bacteria, which comprises applying to at least one of correspondingly (a) such arthropods, (b) such fungi, (c) such bacteria, and (d) the corresponding habitat thereof, i.e. the locus to be protected, e.g. to a growing crop, to an area where a crop is to be grown or to a domestic animal, a correspondingly combative or toxic amount, i.e., an arthropodicidally, fungicidally or bactericidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, dry dressing, moist dressing, wet dressing, slurry dressing, encrusting, and the like.

It will be realized, of course, that the concentration of the particular active compound utilized in admixture with the carrier vehicle will depend upon the intended application. Therefore, in special cases it is possible to go above or below the aforementioned concentration ranges.

The preparation of the new compounds of the present invention is illustrated, without limitation, by the following examples:

EXAMPLE 1

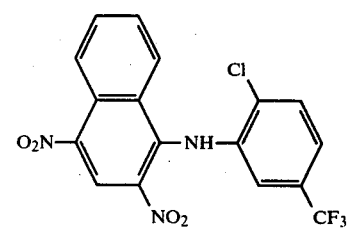
(1)

6.0 g (107 mmols) of pulverulent potassium hydroxide were added, in portions, to a solution of 11.73 g (60 mmols) of 3-amino-4-chloro-benzotrifluoride in 60 ml of dry dimethylformamide at room temperature. A solution of 15.15 g (60 mmols) of 1-chloro-2,4-dinitronaphthalene in 100 ml of dry dimethylformamide was then added dropwise at 25° C. After stirring for three days at room temperature the mixture was filtered and the filtrate was diluted with 50 ml of glacial acetic acid and poured out onto water/ice. 17.6 g of a yellow product were filtered off, from which 11.8 g of 1-(2-chloro-5-trifluoromethyl-phenylamino)-2,4-dinitronaphthalene were obtained, in the form of golden yellow flakes, by recrystallization from isopropanol. Melting point 153° C.

EXAMPLE 2

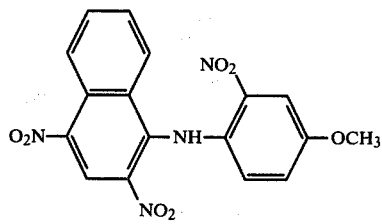

(2)

A mixture of 3.70 g (66 mmols) of potassium hydroxide and 3.71 g (10 mmols) of triphenylethylphosphonium bromide in 50 ml of water, together with 15.15 g (60 mmols) of 1-chloro-2,4-dinitronaphthalene and 10.2 g (60 mmols) of 3-nitro-4-aminoanisole in 150 ml of toluene was stirred for 8 hours at 80° C. 20 g of potassium hydroxide were added and stirring was continued for 5 hours at 80° C. After the mixture had cooled, a dark powder was filtered off, washed with water and water/acetone (12:1) and dissolved in 100 ml of hot glacial acetic acid. A few drops of concentrated hydrochloric acid were added and after cooling 15.0 g of 1-(2-nitro-4-methoxy-phenylamino)-2,4-dinitronaphthalene of melting point 173° C. were isolated. Molecular weight 384 (determined by mass spectrometry).

EXAMPLE 3

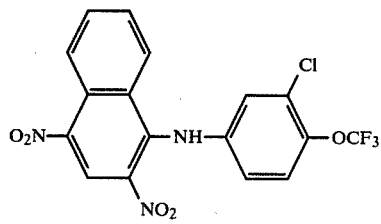

(3)

A suspension of 12.7 g (60 mmols) of 3-chloro-4-trifluoromethoxyaniline and 15.15 g (60 mmols) of 1-chloro-2,4-dinitronaphthalene in 150 ml of water was heated to the boil. 5.6 g (67 mmols) of sodium bicarbonate were introduced in the course of 30 minutes and heating was continued for 2 hours under reflux. After the mixture had cooled to 20° C., the product was filtered off. 24 g of 1-(3-chloro-4-trifluoromethoxy-phenylamino)-2,4-dinitronaphthalene of melting point 140° C. were obtained; after recrystallization from ethanol, 17.4 g of melting point 159° C. were obtained.

EXAMPLE 4

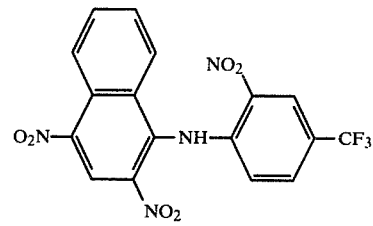

(4)

A solution of 14.0 g of 2,4-dinitro-1-naphthylamine in 50 ml of dimethylformamide was added dropwise, at 0° C., to a suspension of 2.88 g of 80% strength sodium hydride (20% paraffin) in 30 ml of dry dimethylformamide. The mixture was allowed to come to room temperature and was stirred for 1 hour. A solution of 12.55 g of 4-fluoro-3-nitrobenzotrifluoride in 30 ml of dimethylformamide was then added dropwise at 10° C. The batch was stirred overnight at room temperature and a further 0.3 g of 80% strength sodium hydride and 1.25 g of 4-fluoro-3-nitrobenzotrifluoride were added. After stirring for 24 hours, the mixture was filtered, 500 ml of glacial acetic acid were added to the filtrate and the whole was poured out onto 400 g of ice. The yellow precipitate of 1-(2-nitro-4-trifluoromethylphenylamino)-2,4-dinitronaphthalene was filtered off and dried; 21.2 g of melting point 145° C. After recrystallization from amyl alcohol, the melting point rose to 159°–160° C.

EXAMPLE 5

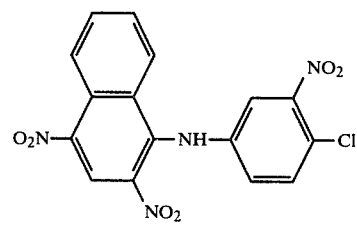

(5)

A solution of 17.3 g (0.1 mol) of 4-chloro-3-nitroaniline in 200 ml of dimethylformamide was added at 0° C. to a suspension of 5 g of sodium hydride (coated with 20% of paraffin) in 100 ml of dimethylformamide. The mixture was stirred for 1 hour at 25° C. and was then cooled to 10° C., and a solution of 25.3 g (0.1 mol) of 1-chloro-2,4-dinitronaphthalene in 250 ml of dimethylformamide was added dropwise. After standing overnight, the mixture was filtered, mixed with 500 ml of glacial acetic acid and poured onto ice. The crystals of 1-(3-nitro-4-chlorophenylamino)-2,4-dinitronaphthalene were filtered off and washed with ether. Yield 25 g, melting point 182° C.

The following compounds could be prepared analogously to Example 5:

Table 1

Structure (VI): Naphthalene with $O_2N$–, $NO_2$–, and –NH–AR substituents

| Compound No. | Ar | Melting point (°C.) |
|---|---|---|
| 6 | 3,4,5-trichlorophenyl (Cl, Cl, Cl) | 174 |
| 7 | 2-CF₃-4,6-dinitrophenyl (CF₃, NO₂, NO₂) | 167 |
| 8 | 3-Br-4-NO₂-phenyl (Br, NO₂) | 199 |
| 9 | 3-Cl-4-NO₂-phenyl (Cl, NO₂) | 169 |
| 10 | 2-NO₂-4-Cl-phenyl (NO₂, Cl) | 191 |
| 11 | 2-NO₂-4,5-dichlorophenyl (NO₂, Cl, Cl) | 186 |
| 12 | 2,4-dinitro-5-bromophenyl (NO₂, NO₂, Br) | 197 |
| 13 | 2-CH₃-3-NO₂-4-Cl-phenyl (CH₃, NO₂, Cl) | 228 |
| 14 | 2-OCH₃-4-NO₂-5-Cl-phenyl (OCH₃, NO₂, Cl) | 258 |
| 15 | 2-NO₂-4-CH₃-phenyl (NO₂, CH₃) | 195 |
| 16 | 2,6-dichlorophenyl (Cl, Cl) | 177–78 |
| 17 | 2,6-dinitrophenyl (NO₂, NO₂) | 200 |
| 18 | 2-Cl-4-NO₂-phenyl (Cl, NO₂) | 192 |
| 19 | 3-Cl-4-F-phenyl (Cl, F) | 132 |
| 20 | 2,4-difluorophenyl (F, F) | 166 |
| 21 | 2-CF₃-phenyl (CF₃) | 146 |
| 22 | 2,4-bis(CF₃)-phenyl (CF₃, CF₃) | 183 |
| 23 | 2-CF₃-4-NO₂-phenyl (CF₃, NO₂) | 184–85 |
| 24 | 4-NO₂-phenyl (NO₂) | 219 |

Table 1-continued

Structure (VI): 1,4-disubstituted naphthalene with $O_2N$- at 5-position, $NO_2$ at adjacent position, and $NH-Ar$ substituent.

| Compound No. | Ar | Melting point (°C.) |
|---|---|---|
| 25 | 2,4-dichloro-5-nitrophenyl (Cl, Cl, $NO_2$) | 210 |
| 26 | 2-cyano-4-nitrophenyl (CN, $NO_2$) | 216 |
| 27 | 2-cyano-5-bromo-4-nitrophenyl (CN, $NO_2$, Br) | 212 |
| 28 | 2-cyano-3,5-dinitrophenyl (CN, $NO_2$, $NO_2$) | 239 |
| 29 | 2-trifluoromethyl-5-bromo-4-nitrophenyl ($CF_3$, $NO_2$, Br) | 196 |
| 30 | 2-methylsulfonyl-4-nitrophenyl ($SO_2CH_3$, $NO_2$) | 248 |
| 31 | 4-methylsulfonylphenyl ($SO_2CH_3$) | 228 |
| 32 | 4-ethoxyphenyl ($OC_2H_5$) | 155–56 |
| 33 | 3-sulfonatophenyl ($SO_3Na$) | 110–113 (free acid) |
| 34 | 4-acetamidophenyl ($NH-COCH_3$) | 252–53 |
| 35 | 2,4-dicyanophenyl (CN, CN) | 236 |
| 36 | 2,4,6-trichlorophenyl (Cl, Cl, Cl) | 199 |
| 37 | 2,6-dichloro-4-trifluoromethylphenyl (Cl, Cl, $CF_3$) | 181 |
| 38 | 2-(tetrafluorodioxomethylene) substituted phenyl | 184 |
| 39 | 2-chloro-4-trifluoromethylthiophenyl (Cl, $SCF_3$) | 190 |
| 40 | 4-trifluoromethoxyphenyl ($OCF_3$) | 159 |
| 41 | 2-trifluoromethyl-4-chlorophenyl ($CF_3$, Cl) | 198 |
| 42 | 2-trifluoromethyl-4-methoxyphenyl ($CF_3$, $OCH_3$) | 219–220 |
| 43 | 3-nitro-4-ethoxyphenyl ($NO_2$, $OC_2H_5$) | 208–209 |
| 44 | 2-chloro-4-trifluoromethylphenyl (Cl, $CF_3$) | 163–165 |

Table 1-continued (VI)

O₂N— [naphthalene structure] —NH—AR
          |
          NO₂

| Compound No. | Ar | Melting point (°C.) |
|---|---|---|
| 45 | 3,5-bis(CF₃)phenyl | 165-167 |
| 46 | 4-NO₂-phenyl-N=N-phenyl | 208-209 |
| 47 | 3,5-diBr-phenyl-N=N-phenyl | 216-218 |
| 48 | 3-CF₃-4-Cl-phenyl | 184 |
| 49 | 4-CN-3-CF₃-phenyl | 157-158 |
| 50 | 2,3,5,6-tetraCl-4-CF₃-phenyl | 211 |

The pesticidal activity of the compounds of this invention is illustrated by the following biotest examples wherein the compounds according to the present invention are each identified by the number (given in brackets) from the examples hereinabove.

The known comparison compounds are identified as follows:

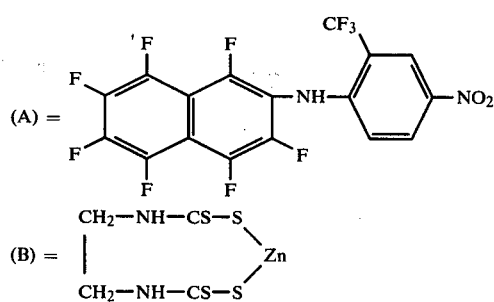

(A) = octafluoronaphthyl-NH-(3-CF₃-4-NO₂-phenyl)

(B) = Zn ethylenebisdithiocarbamate (CH₂—NH—CS—S)₂Zn

EXAMPLE 6

Phaedon larvae test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

Table 2

(Insects which damage plants)
*Phaedon* larvae test

| Active compounds | Active compound concentration in % | Degree of destruction in % after 3 days |
|---|---|---|
| (A) | 0.1 | 20 |
|  | 0.01 | 0 |
| (36) | 0.1 | 100 |
|  | 0.01 | 100 |
| (6) | 0.1 | 100 |
|  | 0.01 | 70 |
| (11) | 0.1 | 100 |
|  | 0.01 | 90 |
| (37) | 0.1 | 100 |
|  | 0.01 | 100 |
| (45) | 0.1 | 100 |
|  | 0.01 | 100 |
| (49) | 0.1 | 100 |
|  | 0.01 | 100 |
| (4) | 0.1 | 100 |
|  | 0.01 | 95 |
| (9) | 0.1 | 100 |
|  | 0.01 | 90 |
| (25) | 0.1 | 100 |
|  | 0.01 | 90 |
| (23) | 0.1 | 100 |
|  | 0.01 | 100 |
| (29) | 0.1 | 100 |
|  | 0.01 | 100 |
| (8) | 0.1 | 100 |
|  | 0.01 | 90 |
| (26) | 0.1 | 100 |
|  | 0.01 | 95 |

EXAMPLE 7

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentration of the active compounds, the evaluation times and the results can be seen from the following table:

Table 3

(Mites which damage plants)
Tetranychus test

| Active compounds | Active compound concentration in % | Degree of destruction in % after 2 days |
| --- | --- | --- |
| (A) | 0.1 | 0 |
| (44) | 0.1 | 100 |
| (45) | 0.1 | 100 |
| (4) | 0.1 | 99 |

EXAMPLE 8

Fusicladium test (apple)/protective

Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20 degrees C. and at a relative atmospheric humidity of 70%. They were then inoculated with an aqueous conidium suspension of the apple scab causative organism (Fusicladium dendriticum) and incubated for 18 hours in a humidity chamber at 18°–20° C. and at a relative atmospheric humidity of 100%.

The plants were then brought into a greenhouse again for 14 days.

15 days after inoculation, the infection of the seedlings was determined. The assessment data were converted to percent infection. 0% meant no infection; 100% meant that the plants were totally infected.

The active compounds, the concentrations of the active compounds and the results can be seen from the following table:

Table 4

Fusicladium test (apple)/protective

| Active compound | Infection in % at an active compound concentration of 0.0025% |
| --- | --- |
| (A) | 32 |
| (26) | 19 |
| (4) | 2 |
| (36) | 20 |
| (6) | 7 |
| (9) | 20 |
| (7) | 2 |
| (33) | 17 |

EXAMPLE 9

Uromyces test (bean rust)/protective

Solvent: 4.7 parts by weight of acetone
Emulsifier: 0.3 part by weight of alkylaryl polyglycol ether
Water: 95 parts by weight The amount of active compound required for the desired concentration of active compound in the spray liquor was mixed with the stated amount of the solvent and the concentrate was diluted with the stated amount of water which contained the stated amount of emulsifier.

The young bean plants, which were in the 2-leaf stage, were sprayed with the spray liquor until dripping wet. The plants remained in a greenhouse for 24 hours at 20°–22° C. and a relative atmospheric humidity of 70% in order to dry. They were then inoculated with an aqueous uredospore suspension of the causative organism of bean rust (Uromyces phaseoli) and incubated for 24 hours in a dark humidity chamber at 20°–22° C. and 100% relative atmospheric humidity.

The plants were then set up in a greenhouse under intensive illumination for 9 days at 20°–22° C. and a relative humidity of 70–80%.

10 days after the inoculation, the infection of the plants was determined. The assessment data were converted to % infection. 0% denoted no infection and 100% denoted that the plants were completely infected.

The active compounds, active compound concentrations and results can be seen from the following table:

Table 5

Uromyces test/protective

| Active compound | Infection in % at an active compound concentration of 0.001% |
| --- | --- |
| (A) | 19 |
| (26) | 2 |
| (4) | 9 |
| (30) | 12 |

EXAMPLE 10

Phytophthora test (tomato)/protective

Solvent: 4.7 parts by weight of acetone
Emulsifier: 0.3 part by weight of alkylaryl polyglycol ether
Water: 95 parts by weight The amount of the active compound required for the desired concentration of the active compound in the spray liquid was mixed with the stated amount of solvent and the concentrate was diluted with the stated amount of water which contained the stated additions.

Young tomato plants with 2 to 4 foliage leaves were sprayed with the spray liquid until dripping wet. The plants remained in a greenhouse for 24 hours at 20° C. and at a relative atmospheric humidity of 70%. The tomato plants were then inoculated with an aqueous spore suspension of Phytophthora infestans. The plants were brought into a moist chamber with an atmospheric humidity of 100% and a temperature of 18°–20° C.

After 5 days the infection of the tomato plants was determined. The assessment data were converted to percent infection: 0% meant no infection; 100% meant that the plants were totally infected.

The active compounds, the concentrations of the active compound and the results can be seen from the following table:

Table 6

Phytophthora test (tomatoes)/protective

| Active compound | Infection in % at an active compound concentration of 0.001% |
|---|---|
| (B) | 44 |
| (26) | 1 |

EXAMPLE 11

Shoot tretment test/cereal rust
(leaf-destructive mycosis)/protective

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20° C. and 100% relative atmospheric humidity.

After 10 days' dwell time of the plants at a temperature of 20° C. and 80–90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The active compound was the more active, the lower was the degree of rust infection.

The active compounds, active compound concentrations in the spray liquor and degrees of infection can be seen from the table which follows:

Table 7

Shoot treatment test/cereal rust/protective

| Active compounds | Active compound concentration in the spray liquor in % by weight | Infection in % of the untreated control |
|---|---|---|
| untreated | — | 100 |
| (A) | 0.01 | 50.0 |
| (23) | 0.01 | 27.5 |
| (4) | 0.01 | 21.3 |
| (36) | 0.01 | 33.8 |
| (37) | 0.01 | 5.0 |
| (45) | 0.01 | 3.8 |
| (49) | 0.01 | 33.8 |
| (6) | 0.01 | 21.3 |
| (8) | 0.01 | 21.3 |
| (9) | 0.01 | 28.8 |
| (3) | 0.01 | 28.8 |
| (38) | 0.01 | 16.3 |

EXAMPLE 12

Pyricularia and Pellicularia test

Solvent: 11.75 parts by weight of acetone
Dispersing agent: 0.75 parts by weight of alkylaryl polyglycol ether
Water: 987.50 parts by weight The amount of active compound required for the desired concentration of active compound in the spray liquid was mixed with the stated amount of the solvent and of the dispersing agent and the concentrate was diluted with the stated amount of water.

2×30 rice plants about 2–4 weeks old were sprayed with the spray liquid until dripping wet. The plants remained in a greenhouse at temperatures of 22° to 24° C. and a relative atmospheric humidity of about 70% until they were dry. Thereafter, the plants were inoculated with an aqueous suspension of 100,000 to 200,000 spores/ml of *Pyricularia oryzae* and placed in a chamber at 24° to 26° C. and 100% relative atmospheric humidity.

Other rice plants, which had been sprayed and dried in the above-described manner, were infected with a culture of *Pellicularia sasakii* grown on malt agar and were set up at 28° to 30° C. and 100% relative atmospheric humidity.

5 to 8 days after the inoculation, the infection of all the leaves present at the time of inoculation with *Pyricularia oryzae* was compared with that of the untreated but also inoculated control plants.

In the case of the plants infected with *Pellicularia sasakii*, the infection at the leaf sheaths after the same time was determined, again in relation to the untreated but infected control.

The evaluation was made on a scale of from 1 to 9. 1 denoted 100% action, 3 denoted good action, 5 denoted moderate action and 9 denoted no action.

The active compounds, the concentrations of the active compounds and the results can be seen from the table which follows.

Table 8

| Pyricularia (a) and Pellicularia (b) test | | |
|---|---|---|
| Active compound | Action at an active compound concentration of 0.025% | |
| | (a) | (b) |
| (A) | 5 | 2 |
| (4) | — | 2 |
| (36) | 3 | — |
| (37) | — | 1 |
| (45) | — | 1 |
| (49) | 5 | 2 |
| (8) | — | 1 |
| (9) | 3 | — |
| (10) | 3 | — |

EXAMPLE 13

Mycelium growth test

Nutrient medium used:
 20 parts by weight of agar-agar
 200 parts by weight of potato decoction
 5 parts by weight of malt
 15 parts by weight of dextrose
 5 parts by weight of peptone
 2 parts by weight of disodium hydrogen phosphate
 0.3 part by weight of calcium nitrate
Ratio of solvent mixture to nutrient medium:
 2 parts by weight of solvent mixture
 100 parts by weight of agar nutrient medium
Composition of the solvent mixture:
 0.19 part by weight of dimethylformamide 0.01 part by weight of emulsifier (alkylaryl polyglycol ether)

1.80 parts by weight of water

The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified, the plates were inoculated with the species of fungi stated in the table and incubated at about 21° C.

Evaluation was carried out after 4–10 days, dependent upon the speed of growth of the fungi. When evaluation was carried out the radial growth of the mycelium on the treated nutrient media was compared with the growth on the control nutrient medium. In the evaluation of the fungus growth, the following characteristic values were used:

1 no fungus growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

Table 9

Mycelium growth test

| Active compounds (concentration = 10 ppm) | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum | Pyricularia oryzae | Phialophora cinerescens | Helminthosporium gramineum | Mycosphaerella musicola | Phytophthora cactorum | Venturia inaequalis | Pellicularia sasakii | Xanthomonas oryzae |
|---|---|---|---|---|---|---|---|---|---|---|---|---|---|---|---|---|---|
| (B) | 9 | 9 | 9 | 9 | 9 | 5 | 9 | 9 | 9 | 9 | 9 | 5 | 5 | 9 | — | 9 | 9 |
| (23) | 5 | 5 | 5 | — | 5 | 2 | 9 | — | — | — | — | 5 | — | — | — | 5 | 3 |
| (29) | — | 5 | 3 | 5 | — | 3 | — | 5 | 5 | 1 | — | 1 | — | — | — | 1 | — |
| (4) | 5 | — | — | — | — | — | 3 | — | 5 | — | — | 3 | — | — | — | — | — |
| (36) | 5 | — | 3 | — | — | 1 | 3 | — | — | 1 | — | 5 | — | — | — | — | — |
| (37) | — | — | 3 | — | — | — | — | 3 | — | — | — | — | — | — | — | — | — |
| (49) | 3 | 3 | 3 | — | — | 3 | 5 | 5 | — | — | 1 | 2 | 2 | 1 | — | 1 | 2 |
| (8) | 5 | — | — | — | — | 3 | 5 | 5 | 5 | — | 5 | 1 | 1 | 1 | — | — | — |
| (9) | 3 | — | — | — | — | 5 | — | — | — | — | — | 1 | — | — | — | — | — |
| (10) | — | 1 | — | — | 3 | — | — | — | — | — | — | — | — | — | — | — | — |
| (11) | 5 | — | — | — | 2 | — | — | — | — | 5 | — | — | — | — | — | — | — |

EXAMPLE 14

Bacteria test/*Xanthomonas oryzae*

Solvent: 11.75 parts by weight of acetone
Dispersing agent: 0.75 part by weight of alkylaryl polyglycol ether
Water: 987.50 parts by weight The amount of active compound required for the desired active compound concentration in the spray liquor was mixed with the stated amount of the solvent and of the dispersing agent and the concentrate was diluted with the stated amount of water.

30 rice plants which were about 40 days old were sprayed with the spray liquor until dripping wet. The plants remained in a greenhouse, at temperatures of 22° to 24° C. and a relative atmospheric humidity of about 70%, until they had dried. Needles were then dipped into an aqueous bacterial suspension of *Xanthomonas oryzae* and the plants were inoculated by pricking the leaves. After the inoculation, the leaves stood for 24 hours at 100% relative atmospheric humidity and thereafter in a room at 26° to 28° C. and 80% relative atmospheric humidity.

10 days after the inoculation, the infection of all pricked inoculated leaves of plants which had beforehand been treated with the preparation was evaluated, using a scale of from 1 to 9. 1 denoted 100% action, 3 denoted a good action, 5 denoted a moderate action and 9 denoted no action.

The active compounds, active compound concentrations and results can be seen from the table which follows:

Table 10

| Bacteria test/ *Xanthomonas oryzae* | |
|---|---|
| Active compound | Action at an active compound concentration of 0.025% |
| (A) | 9 |
| (37) | 3 |
| (1) | 5 |
| (5) | 5 |
| (32) | 3 |
| (33) | 3 |
| (31) | 5 |
| (3) | 5 |
| (42) | 5 |
| (43) | 5 |
| (2) | 5 |
| (46) | 3 |

The experiments given below show the arthropod development-inhibiting action of the compounds according to the invention without intending to imply a limitation in respect of the breadth of action of these compounds. In these tests, the morphological changes, such as partially pupated animals, incompletely slipped larvae or caterpillars, defective wings, pupal cuticula in imagines and the like were assessed as mis-developments over the entire stated development of the test insects.

EXAMPLE 15

Development-inhibiting action/ingestion test

Test insects: *Plutella maculipennis* (caterpillars in the 4th stage of development, 20 specimens)
Feed plants: Cabbage plants (*Brassica oleracea*)
Solvent: 4 parts by weight of acetone
Emulsifier: 1 part by weight of alkylaryl polyglycol ether To produce a suitable preparation of active compound, 2 parts by weight of active compound were mixed with the stated amount of solvent, emulsifier and sufficient water to give a 1% strength mixture, which was diluted with water to the desired concentration.

The test insects were fed with leaves of the feed plants, which were provided with a uniform spray covering of the active compound mixture of the desired concentrations, so that the stated amounts of active compound in ppm (parts per million) were obtained on the leaves, until the imago developed.

As a control, leaves provided only with solvent and emulsifier of the stated concentration were used as the feed.

The sum of the morphological malformations and of the destruction was determined as a percentage. 100% meant that all of the insects were either killed or morphologically damaged while 0% meant that no damage had taken place.

The results can be seen from the table which follows:

Table 11

| Development-inhibiting action/ingestion test | | |
|---|---|---|
| Active compound | *Plutella macul.* 10 ppm | 1 ppm |
| Control (untreated) | 0% | 0% |
| (A) | 100% | 50% |
| (26) | 100% | 100% |
| (27) | 100% | 100% |
| (28) | 100% | 100% |
| (29) | 100% | 70% |
| (30) | 100% | 70% |
| (35) | 100% | 60% |
| (4) | 100% | 100% |
| (36) | 100% | 100% |
| (22) | 100% | 100% |

EXAMPLE 16

Development-inhibiting action

Test insect: *Ceratitis capitata* (20 eggs)
Feed: Artificial feed (carrot powder and yeast powder)
Solvent: 20 parts by weight of acetone
Emulsifier: 5 parts by weight of alkylaryl polyglycol ether To produce a suitable preparation of active compound, 4 parts by weight of active compound were mixed with the stated amount of solvent, emulsifier and sufficient water to give a 1% strength mixture which was diluted with water to the desired concentration.

The eggs of the test insect were placed on a dish with the artificial feed, into which the chosen concentration of the active compound mixture had been incorporated so that the stated amount of active compound in ppm (parts per million) was achieved. The development was observed until the flies slipped.

As a control, artificial feed mixed only with solvent and emulsifier of the stated concentration was offered.

The sum of the morphological malformations and of the destruction was determined as a percentage. 100% meant that all of the insects were either killed or morphologically damaged while 0% meant that no damage had taken place.

The results can be seen from the table which follows:

Table 12

| | Development-inhibiting action Test insects: *Ceratitis capitata* | |
|---|---|---|
| Active compound | Damage at a concentration of 10 ppm | |
| Control (untreated) | 0% | |
| (A) | 20% | |
| (22) | 100% | |
| (26) | 100% | |
| (30) | 100% | |

EXAMPLE 17

Development-inhibiting action

Test insect: *Aedes aegypti* (larvae in the 3rd stage of development, 20 specimens)
Solvent: 10 parts by weight of acetone
Emulsifier: 1 part by weight of polyoxyethylene-(20) sorbitan monolaurate To produce a suitable preparation of active compound, 2 parts by weight of active compound were mixed with the stated amount of solvent, emulsifier and sufficient water to produce a mixture containing 10 ppm, which was diluted with water to the desired concentration.

The test insects were introduced into 90 ml of these active compound solutions and were observed until the imago slipped. As a control, test insects were introduced into a solvent/emulsifier/water mixture of the stated concentration and observed until the imago slipped.

The sum of the morphological malformations and of the destruction was determined as a percentage. 100% meant that all of the insects were either killed or morphologically damaged while 0% meant that no damage had take place.

The results can be seen from the table which follows:

Table 13

| | Development-inhibiting action/ mosquito test Test insects: *Aedes aegypti* | |
|---|---|---|
| Active compound | Damage at a concentration of 0.1 ppm | |
| Control (untreated) | 0% | |
| (A) | 0% | |
| (25) | 100% | |
| (26) | 100% | |
| (28) | 100% | |
| (30) | 100% | |

It will be appreciated that the instant specification and examples are set forth by way of illustration and not limitation, and that various modifications and changes may be made without departing from the spirit and scope of the present invention.

What we claim is:

1. A 1-arylamino-2,4-dinitronaphthalene selected from the group consisting of
1(2-cyano-4-nitro-phenylamino)-2,4-dinitronaphthalene,
1-(2-cyano-4,6-dinitro-phenylamino)-2,4-dinitronaphthalene,
1-(2-methylsulfonyl-4-nitro-phenylamino)-2,4-dinitronaphthalene,
1-(2-nitro-4-trifluoromethyl-phenylamino)-2,4-dinitronaphthalene,
1-(3,5-bis-trifluoromethyl-phenylamino)-2,4-dinitronaphthalene,
1-(2-nitro-4,6-dichlorophenylamino)-2,4-dinitronaphthalene, and
1-(2,4-trifluoromethylphenylamino)-2,4-dinitronaphthalene.

2. A compound according to claim 1, wherein such compound is 1-(2-cyano-4-nitro-phenylamino)-2,4-dinitronaphthalene of the formula

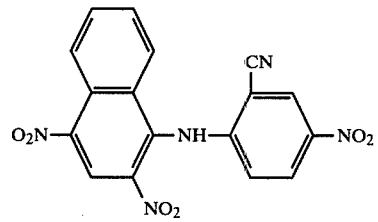

3. A compound according to claim 1, wherein such compound is 1-(2-cyano-4,6-dinitro-phenylamino)-2,4-dinitronaphthalene of the formula

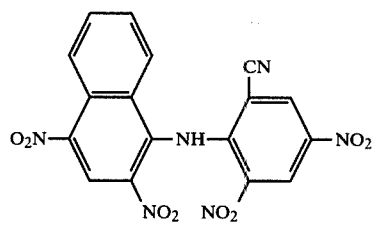

4. A compound according to claim 1, wherein such compound is 1-(2-methylsulfonyl-4-nitro-phenylamino)-2,4-dinitronaphthalene of the formula

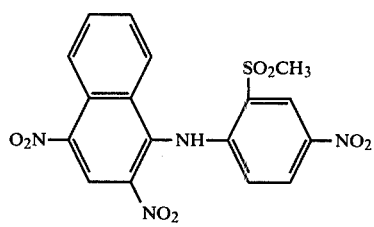

5. A compound according to claim 1, wherein such compound is 1-(2-nitro-4-trifluoromethyl-phenylamino)-2,4-dinitronaphthalene of the formula

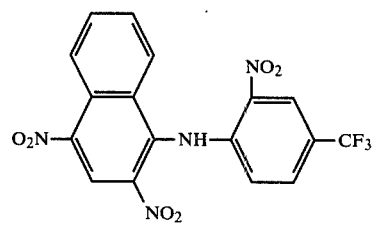

6. A compound according to claim 1, wherein such compound is 1-(3,5-bis-trifluoromethyl-phenylamino)-2,4-dinitronaphthalene of the formula

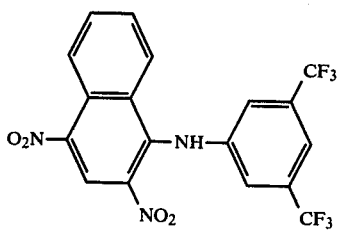

7. A compound according to claim 1, wherein such compound is 1-(2-nitro-4,6-dichlorophenylamino)-2,4-dinitronaphthalene of the formula

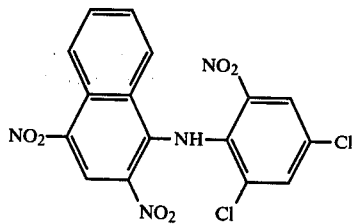

8. A compound according to claim 1 wherein such compound is 1-(2,4-trifluoromethylphenylamino)-2,4-dinitronaphthalene of the formula

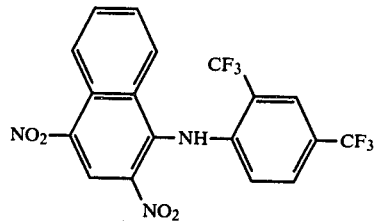

9. An arthropodicidal, fungicidal or bactericidal composition containing as active ingredient an arthropodicidally, fungicidally or bactericidally effective amount of a compound according to claim 1 in admixture with a solid diluent.

10. A method of combating arthropods, fungi or bacteria which comprises applying to the anthropods, fungi or bacteria, or to a habitat thereof, an arthopodically, fungicidally or bactericidally effective amount of
- 1-(2-cyano-4-nitro-phenylamino)-2,4-dinitronaphthalene,
- 1-(2-cyano-4,6-dinitro-phenylamino)-2,4-dinitronaphthalene,
- 1-(2-methylsulfonyl-4-nitro-phenylamino)-2,4-dinitronaphthalene,
- 1-(2-nitro-4-trifluoromethyl-phenylamino)-2,4-dinitronaphthalene,
- 1-(3,5-bis-trifluoromethyl-phenylamino)-2,4-dinitronaphthalene,
- 1-(2-nitro-4,6-dichlorophenylamino)-2,4-dinitronaphthalene, or
- 1-(2,4-trifluoromethylphenylamino)-2,4-dinitronaphthalene.

* * * * *